United States Patent
Wissink et al.

(10) Patent No.: US 9,802,013 B2
(45) Date of Patent: Oct. 31, 2017

(54) INHALER WITH A MIXING CHANNEL FOR PRODUCING AN AEROSOL TO BE INHALED

(75) Inventors: Jeroen Mathijn Wissink, DW Enschede (NL); Wietze Nijdam, JE Zutphen (NL); Iwan Rutger Heskamp, PT Enschede (NL); Marc Herman Padberg, RM Enschede (NL)

(73) Assignee: MEDSPRAY XMEMS BV, DW Enschede (NL)

(*) Notice: Subject to any disclaimer, the term of this patent is extended or adjusted under 35 U.S.C. 154(b) by 2655 days.

(21) Appl. No.: 11/885,807

(22) PCT Filed: Mar. 9, 2006

(86) PCT No.: PCT/EP2006/002154
§ 371 (c)(1),
(2), (4) Date: May 12, 2008

(87) PCT Pub. No.: WO2006/094796
PCT Pub. Date: Sep. 14, 2006

(65) Prior Publication Data
US 2009/0050137 A1 Feb. 26, 2009

(30) Foreign Application Priority Data
Mar. 10, 2005 (DE) .................. 10 2005 010 965

(51) Int. Cl.
*A61M 15/00* (2006.01)
*A61M 11/06* (2006.01)
(52) U.S. Cl.
CPC .......... *A61M 15/009* (2013.01); *A61M 11/06* (2013.01); *A61M 2206/10* (2013.01)
(58) Field of Classification Search
USPC .................. 128/200.14, 200.23, 200.18
See application file for complete search history.

(56) References Cited

U.S. PATENT DOCUMENTS 3,923,202 A * 12/1975 Riccio .................. 222/145.5
4,148,308 A * 4/1979 Sayer .................. 600/205
(Continued)

FOREIGN PATENT DOCUMENTS

| DE | 43 06 458 | 9/1994 |
| GB | 1 227 333 | 4/1971 |
| WO | 02/18058 | 3/2002 |

OTHER PUBLICATIONS

Schmidt, Atomiser for therapeutic purposes, Sep. 15, 1994, English translation of DE4306458 A1 by the EPO.*

Primary Examiner — Rachel Young
(74) Attorney, Agent, or Firm — Lucas & Mercanti, LLP; Kalus P. Stoffel (57) ABSTRACT

An inhaler with a mixing channel (1) for producing an aerosol to be inhaled includes an outlet (9) at one end that can be inserted in the mouth of a person in order to inhale the aerosol that is produced; at least one inlet (3) at its other end for drawing air into the mixing channel (1); and at least one injection zone (6) that lies between the inlet (3) and the outlet (9) and forms part of the channel wall. The injection zone (6) has at least one nozzle orifice (10) for supplying a liquid, especially a liquid drug, wherein the inner surface of the injection zone (6) is largely flush at least with that portion of the mean surface curvature (22) of the inner surface of the channel wall (11) that is adjacent to it on the inlet end. A possible height difference (17) between the inner surface of the injection zone (6) and that portion of the mean surface curvature (22) of the inner surface of the channel wall (11) that is adjacent to it is less than 1 mm or at most 100 μm or at most 20 μm.

24 Claims, 10 Drawing Sheets (56) References Cited

U.S. PATENT DOCUMENTS

| | | | |
|---|---|---|---|
| 4,592,348 A | | 6/1986 | Waters, IV et al. |
| 5,027,808 A | * | 7/1991 | Rich et al. ............... 128/203.23 |
| 5,522,380 A | * | 6/1996 | Dwork .................... 128/200.23 |
| 5,724,986 A | * | 3/1998 | Jones et al. .................. 600/538 |
| 5,755,218 A | * | 5/1998 | Johansson et al. ...... 128/200.14 |
| 5,896,853 A | * | 4/1999 | Howlett .................. 128/200.23 |
| 6,341,603 B1 | * | 1/2002 | Howlett .................. 128/200.23 |
| 6,447,816 B1 | | 9/2002 | Vail, III et al. |
| 6,581,590 B1 | * | 6/2003 | Genova et al. .......... 128/200.23 |
| 6,615,826 B1 | * | 9/2003 | Gabrio et al. ........... 128/200.23 |
| 7,793,806 B2 | * | 9/2010 | Allsop ....................... 222/402.2 |
| 2003/0041859 A1 | * | 3/2003 | Abrams et al. .......... 128/200.22 |
| 2004/0035417 A1 | * | 2/2004 | Ottolangui ............... 128/202.17 |
| 2005/0005929 A1 | * | 1/2005 | Snyder et al. ........... 128/200.23 |
| 2005/0011524 A1 | * | 1/2005 | Thomlinson et al. ... 128/207.18 |

\* cited by examiner

INHALER WITH A MIXING CHANNEL FOR PRODUCING AN AEROSOL TO BE INHALED

The invention concerns an inhaler with a mixing channel for producing an aerosol to be inhaled, where the mixing channel has: an outlet at one end that can be inserted in the mouth of a person in order to inhale the aerosol that is produced; at least one inlet at its other end for drawing air into the mixing channel; and at least one injection zone that lies between the inlet and the outlet and forms part of the channel wall, where the injection zone has at least one nozzle orifice for injecting a liquid, especially a liquid drug, in the form of one jet of dispersed droplets per nozzle orifice, into the mixing channel so as to entrain the droplets with the stream of intake air and keep them separated in an end zone between the injection zone and the outlet after the droplets have been mixed with the stream of air to form the aerosol.

International Patent Application WO 2002/018058 A1 (FIG. 16) discloses a mixing channel of this type, in which the injection zone is formed by a nozzle plate, which forms an angle of +10° to +90° with the wall or longitudinal center axis of the mixing channel. In this position of the nozzle plate in the mixing channel, air turbulence develops at the edges of the nozzle plate when air is inhaled through the mixing channel. This turbulence reduces the respiratory air flow rate and prevents the very small droplets that form after the emergence of the initially continuous jet from staying separated during the mixing with the air. They can coalesce into larger droplets that are no longer monodisperse and are then unable to penetrate to the desired place, especially the targeted passages of the lung, and are partly deposited on the wall of the channel. This reduces the effectiveness of the liquid or drug.

The objective of the invention is to improve an inhaler of the aforementioned type in such a way that the droplets of liquid, especially a liquid drug, which are contained in the aerosol remain separated when the inhaler is used and penetrate the mouth, throat, and, if necessary, the smallest branches of the lungs without being deposited on the wall of the channel.

In accordance with the invention, this objective is achieved by virtue of the fact that the inner surface of the injection zone is largely flush at least with that portion of the mean surface curvature of the inner surface of the channel wall that is adjacent to it on the inlet end, where a possible height difference between the inner surface of the injection zone and that portion of the mean surface curvature of the inner surface of the channel wall that is adjacent to it is less than 1 mm or at most 100 μm or at most 20 μm.

This solution to the problem largely avoids projecting edges in the mixing channel, which would cause turbulence when air flows around them, which in turn would cause the droplets of liquid to coalesce or to be deposited on the wall of the channel.

The deposition of the aerosol in the respiratory tract is affected not only by the droplet size distribution but also the inhalation flow rate and the inhalation volume. However, the inhalation flow rate and the inhalation volume also depend on the person who is using the inhaler, i.e., on the operating conditions and not only on the design parameters of the mixing channel. Nevertheless, the aerosol is produced by a volume flow of air during inhalation which is greater than the normal flow rate of the respiratory air. This can be realized by means of a passage cross section of the mixing channel that converges or at least is constant up until the injection zone. In this regard, the passage cross section of the channel at the narrowest point is smaller than the normal opening width of the mouth during normal inspiration through the mouth. This contributes to an increase in the flow rate of the aerosol through the mixing channel and to the fact that, on the one hand, the jets (if there are more than one) are separated into monodisperse droplets and, on the other hand, the droplets of the jet or of each jet remain separated from one another, so that the monodisperse nature of the aerosol is largely preserved. Preservation of the monodisperse state of the droplets can be achieved by certain channel characteristics and dimensions.

It can then be provided that the channel wall diverges or converges linearly in the direction of air flow, that the area $A(x)$ of the passage cross section of the mixing channel varies with the distance x from the inlet or from the smallest passage cross section in the injection zone, and that the change $dA(x)/dx$ at the point x is between $-c_1\sqrt{A(x)}$ and 0 or between $c_2\sqrt{A(x)}$ and 0, where $c_1=15.35$ or 4.22, and $c_2=1.58$ or 0.88 or 0.31. This ensures that, even when the shape of the passage cross section changes over the length of the mixing channel, the stream of air does not become detached from the wall of the channel and remains free of turbulence, and that the respiratory air flow rate is minimized. Below $c_2=1.53$ and especially below 0.31, there is no danger that the air will become separated from the channel wall, which would lead to turbulence. In the stream of air, the droplets are kept separated from one another and from the wall of the channel. They retain their original small size with a diameter of about 1-10 μm. The liquid jet is initially continuous as it emerges from the nozzle orifice, namely, with a diameter of about 0.5 to 5 μm, corresponding to the diameter of the nozzle orifice, before it makes the transition to monodisperse droplets (of the same size) a small distance from the nozzle orifice. The droplets undergo hardly any coalescence but rather remain largely monodisperse until they enter the small lung passages or bronchi without being deposited on the wall of the channel. This allows better absorption of the drug in the lung, specifically, about 30% to almost 100%, as opposed to 0 to 30% previously. For example, a larger percentage of relatively small droplets with a diameter of 2 μm would also reach the alveoli when the size distribution of the droplets is monodisperse, and the relatively large droplets of 5 μm would reach the bronchi. Preferably, the geometric standard deviation (GSD) of the diameter of the droplets in the aerosol is adjusted and optimized in such a way that the mass median aerodynamic diameter (MMAD) of the droplets of the aerosol is in the range of 1 to 5 μm, or 1 to at least 10 μm, and ideally the GSD is 1.0.

In one embodiment, the channel wall can be shaped in such a way that the mixing channel converges from the inlet to the injection zone and then diverges again. Due to the divergence of the channel, the initially higher flow rate of the aerosol in the injection zone decreases again, so that it largely adapts to the normal inspiration flow rate, and the droplets are not deposited to a significant extent in the mouth and throat. Alternatively, this can also be accomplished by convergence or constant passage cross section, with the mouth acting as a divergent channel in the latter case.

Another possibility consists in the channel wall converging, with the mixing channel in a horizontal attitude, at least above and below its longitudinal center axis in relation to this in a section that extends beyond the injection zone, and diverging downstream of the convergent section.

In another possible embodiment, with the mixing channel in a horizontal attitude, the channel wall converges like a trumpet from the inlet to the injection zone, at least above and below its longitudinal center axis.

It is most favorable if the axial section contour of the inner surface of the section of the channel wall that converges like a trumpet corresponds to the curve of a parabola of third degree, at least above and below the longitudinal center axis.

In an especially favorable embodiment, the passage cross section of the mixing channel continuously decreases in successive longitudinal sections from a rectangular shape at the inlet to a rectangular shape with rounded corners across the injection zone, and it then makes a transition from rectangular shapes with rounded corners and outwardly arched sides to a circular shape.

It is preferred for the jet to emerge from the injection zone at an angle α to a tangent to the injection zone of 10-170° and preferably 10 to 90° or 90 to 170° and for the jet to have an initial inclination to the outlet of α<90° and an initial inclination to the inlet of α>90°.

The length of a mixing zone that follows the injection zone in the axial direction of the mixing channel can be 1-50 mm.

The length of an end zone that follows the mixing zone can be 2 to 3 times the length of the mixing zone.

The area of the passage cross section of the mixing channel at the end of an inlet zone that extends to the injection zone should be 1 to 1,000 mm$^2$, or 5 to 100 mm$^2$, and preferably 10 to 20 mm$^2$.

The injection zone is preferably formed by a nozzle plate. This allows separate optimum formation of the injection zone in a simple way by suitable shaping of the nozzle plate, specifically, independently of the material of the mixing channel. In particular, it is possible to shape the nozzle orifice(s) favorably by simple means.

For example, when the mixing channel is made of plastic for the sake of easy shaping, but it is found to be difficult to make the nozzle orifice(s) sufficiently small, it is possible to produce the nozzle plate from a material, preferably silicon coated with silicon nitride, in which the nozzle orifices can be made very small, say, with a diameter of 0.5 to 5 μm, and in which it is also possible that the (initial) direction of jet emergence from the channel wall forms the angle α with the tangent to the point of jet emergence. Moreover, the plastic of the mixing channel can contain an antibacterial and/or electrically conductive additive or have a coating that prevents electrostatic charging. The additive can consist of metal, carbon, or graphite particles or a conductive polymer. The coating can be made of metal.

The surface of the inside of the channel wall can then be at least partially microtextured, e.g., by a surface treatment, by a surface coating, or by suitable shaping in an extrusion die. This results in lower friction between the stream of air and the channel wall than in the case of a smooth wall, thereby increasing the air flow.

Coalescence of the droplets can be prevented by maximizing the tensile forces that are exerted on the droplets by the air flow profile and the air flow rate. For example, an air flow resistor can be installed on or in front of the inlet. This device can be a perforated plate with at least one hole. The reason is this: Since the flow resistance of the mixing channel is optimized, a flow rate that is too high can develop when a patient applies a normal suction pressure of 2 to 4 kPa. When an air resistance device is placed in front, the air flow rate is limited. Thus, especially a perforated plate has a nonlinear effect on the air flow rate. A hole in the plate, especially a short, circular hole, results in a greater than proportional, especially quadratic, relationship between the pressure (negative pressure during suction) and the air flow rate. As a result, there is hardly any reduction of the flow rate at low suction force, but when the patient applies maximum suction force, there is a lower flow rate than without an air resistance device. This gives the patient a better feeling when he draws on the inhaler. He can draw the air uniformly for a prolonged period of time.

Provision is preferably made for the metering unit to have a piston-cylinder system for applying pressure to the liquid to be injected into the mixing channel and an actuator that can be moved by manual pressure, whose actuation distance can be converted by a spring mechanism to relative movement between the piston and the cylinder of the piston-cylinder system. In this design, the pressure applied to the liquid, the velocity of the liquid during its injection, and the duration of the injection into the mixing channel depend essentially only on the force of the spring mechanism, which can be closely adjusted to the force necessary to maintain a desired inhalation duration of about 0.5 to 10 seconds and a corresponding velocity of the jet. The user thus has less influence on the actuation pressure, which makes the inhaler easier to use.

In an especially suitable embodiment of the inhaler, it is then possible for the cylinder to be tightly mounted in a closure device of a reservoir that contains the liquid and for it to extend into the reservoir; for a piston rod of the piston to be passed through the closure device; for an outlet channel that extends to the injection zone to be passed through the piston and the piston rod; for the piston rod to be mounted in a housing that displaceably holds the closure device; for the actuation distance of the actuator to be transferred to the closure device by the spring mechanism against the force of another spring mechanism, so that the closure device is moved relative to the piston; for the pressure chamber of the cylinder in the unactuated state of the actuator to be connected with the interior of the reservoir by at least one hole in the wall of the cylinder and by a valve system; and for the hole(s) in the cylinder wall and the valve system to be blocked during the operation of the actuator after the piston has traveled beyond the hole(s) in the cylinder wall.

The invention and its modifications are described in greater detail below with reference to the specific embodiments of the invention that are shown in the accompanying drawings.

FIG. 1 is a schematic side view of an inhaler for producing an aerosol to be inhaled, with a mixing channel of the invention, the mouthpiece of which is inserted in the mouth of a patient to treat his lungs.

FIG. 2 is an enlarged schematic view of a vertical section through the longitudinal center axis of an embodiment of a mixing channel of the invention.

FIG. 3 is a view of a vertical section through the longitudinal center axis of a second embodiment of a mixing channel of the invention.

FIG. 4 is a view of a vertical section through the longitudinal center axis of a third embodiment of a mixing channel of the invention.

FIG. 5 is a view of a vertical section through the longitudinal center axis of a fourth embodiment of a mixing channel of the invention.

FIG. 6 shows a drawing that represents three embodiments of a mixing channel of the invention, which are modifications of the mixing channel illustrated in FIG. 2.

FIG. 7 is a view of a vertical section through the longitudinal center axis of an eighth embodiment of a mixing channel of the invention.

FIG. 8 is a view of a vertical section through the longitudinal center axis of a ninth embodiment of a mixing channel of the invention.

Figure 1:
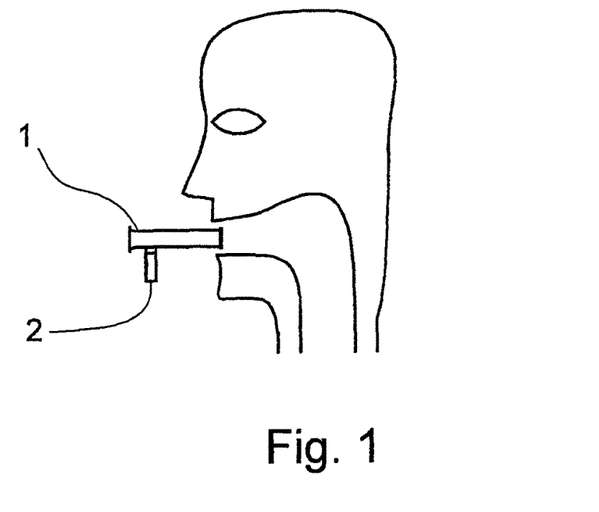
Figure 23:
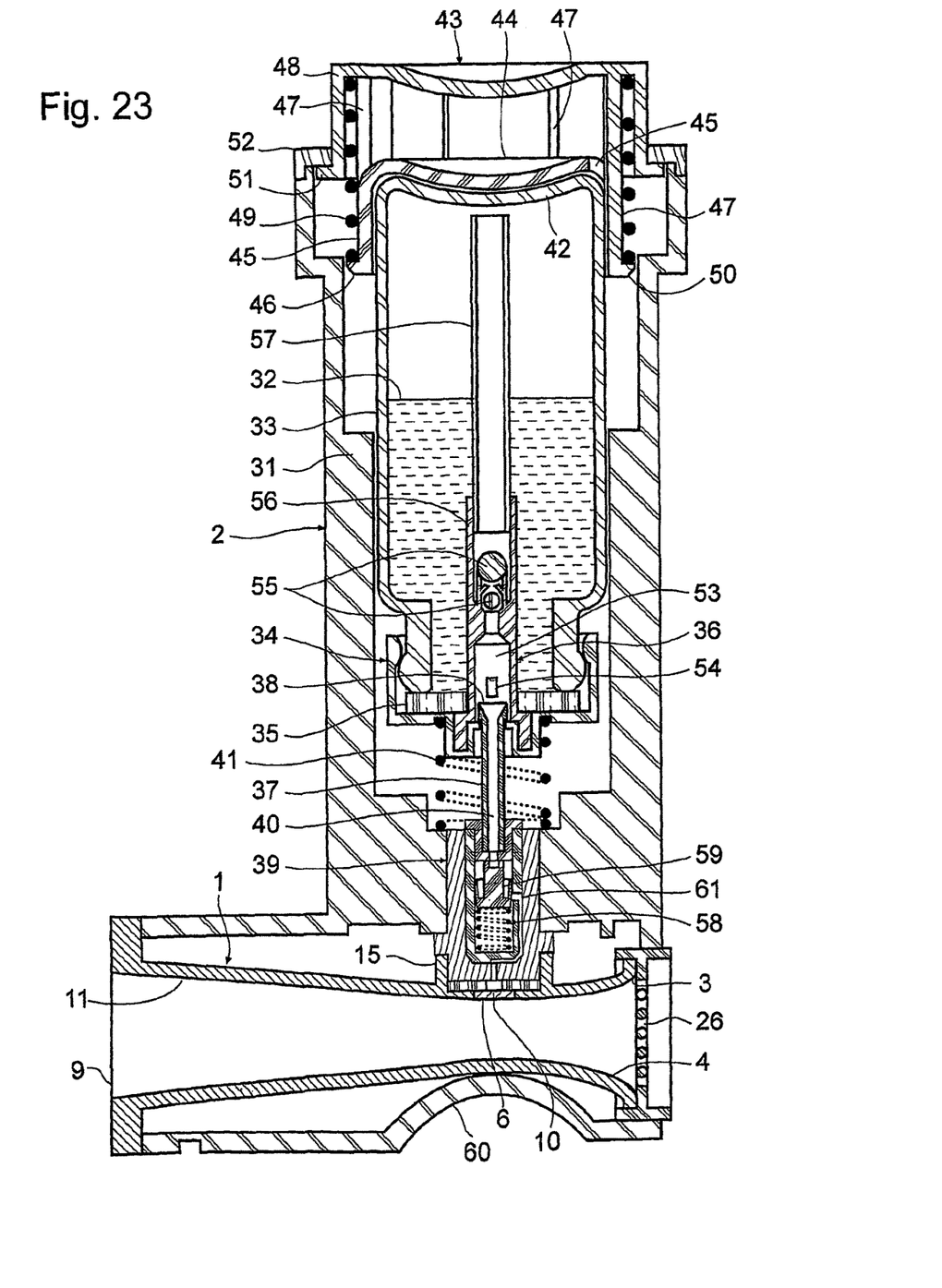
FIG. 23 is a schematic view of a vertical section through the longitudinal center axis of an embodiment of an inhaler of the invention.

The inhaler illustrated in FIG. 1 has a mixing channel 1 in accordance with the invention, which forms a mouthpiece and is inserted in the mouth of a user, such as a patient with pulmonary disease or asthma. A metering unit 2, which in this case has a conventional, manually operated pump, is connected to the mixing channel 1. Alternatively, the metering unit 2 can also be positioned on top of the mixing channel 1, as shown in FIG. 23. A liquid drug is injected into the mixing channel 1 by the metering unit 2 and is mixed in the mixing channel 1 with the respiratory air of the patient to produce an aerosol, which the patient inhales.

Figure 2:
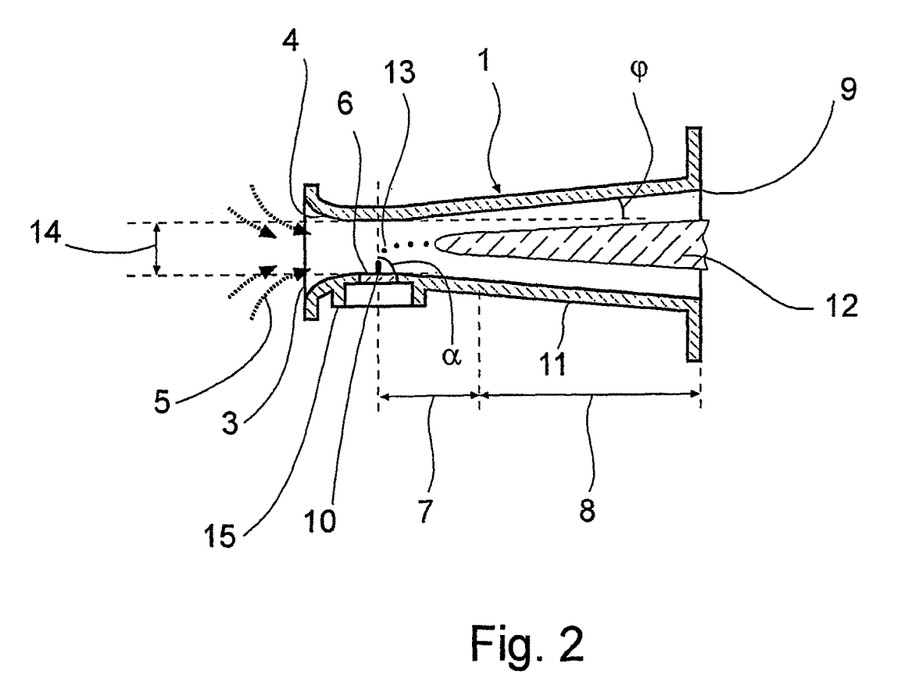

As shown in FIG. 2, when the patient inhales, he draws air 5 into the mixing channel 1 through at least one inlet 3 (only one inlet is shown in the drawing) with a circular passage cross section and through an inlet zone 4 that narrows according to the shape of a trumpet. The air flow then continues through an injection zone 6, which is designed as a nozzle plate, a mixing zone 7, an end zone 8, and an outlet 9. At least one nozzle orifice 10 (again, only one is shown in the drawing) with a very small orifice width of about 0.5 to 5 μm is formed in the injection zone 6. On the selected scale of the drawing, this orifice width is not visible. Upon manual actuation or initiation of the pressure stroke of a piston of a piston-cylinder unit in the metering unit 2, an initially continuous jet of the liquid drug emerges from each nozzle orifice 10 in the injection zone 6 at an angle α to a tangent to the injection zone 6 (vertically in the present case). At only a very small distance from the inner surface of the lower wall 11 (with the mixing channel 1 in a horizontal attitude), the initially continuous jet disintegrates into a stream of very fine droplets 13 with a diameter of about 1 to 10 μm. The droplet diameter depends on the diameter of the nozzle orifice 10. The droplets 13 are entrained by the air flow and are mixed with the air in the mixing zone 7 to form the aerosol 12. A constriction 14 of the mixing channel 1 in the injection zone 6 is designed sufficiently small that, under the conditions of normal suction produced by inhalation, a higher flow rate is imparted to the air in the injection zone 6 than the air entering the inlet 3. This very reliably prevents the droplets 13 from coming into contact with and adhering to the channel wall that lies opposite the injection zone 6. After the constriction 14, the mixing channel 1 diverges at an angle φ relative to its longitudinal center axis (or to a line parallel to its longitudinal center axis). The angle φ is selected less than 24° or 14°, preferably less than 10°, and ideally less than 5°. This prevents the air flow from separating from the channel wall. This in turn prevents the droplets 13 from coalescing due to air turbulence caused by separation of the stream of air from the channel wall and thus from being deposited on the channel wall. Therefore, they remain monodisperse (of equal size) or retain a monodisperse character or a predetermined droplet size distribution. At the same time, the flow rate decreases again, so that the droplets do not enter the oral cavity at an excessively high velocity. This prevents them from adhering to the inside surface of the mouth or the throat without reaching the lungs.

A connecting piece 15 that surrounds the injection zone serves to connect the metering unit 2.

Figure 3:
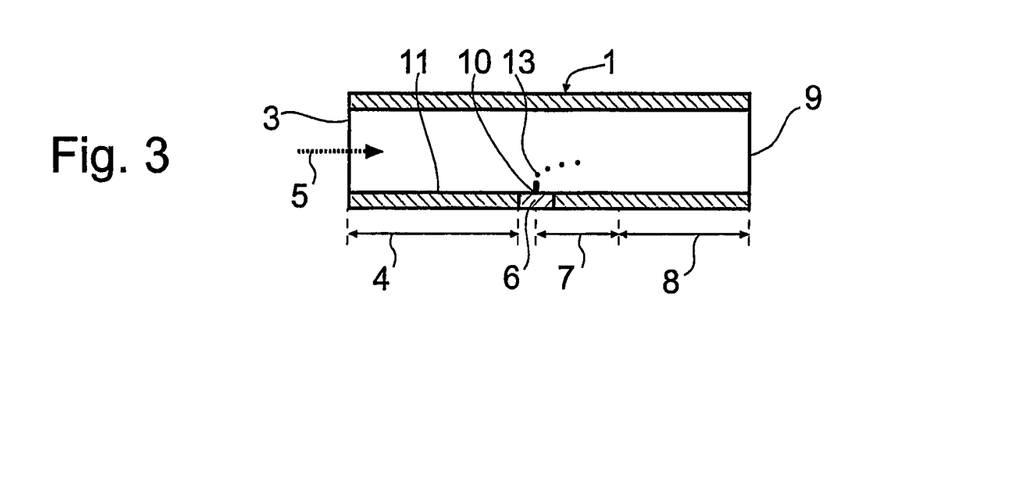

In the embodiment according to FIG. 3, the mixing channel 1 is straight over its entire length. Therefore, the angle φ is equal to 0°. However, its passage diameter is somewhat greater than the passage diameter in the constriction 14 of the mixing channel according to FIG. 2. Its injection zone 6 is located approximately at the midpoint of its length. The position and length of its inlet zone 4 and end zone 7 are correspondingly shifted relative to those of the mixing channel 1 according to FIG. 2 and are lengthened or shortened. The connecting piece 15 can be eliminated and therefore is not shown in FIG. 3. The flow of the air or the aerosol continues free of separation and turbulence beyond the injection zone. Since the air flows somewhat more slowly due to the greater passage cross section, the droplets 13 are likewise prevented from being deposited in the oral cavity or the throat and adhering there.

Figure 4:
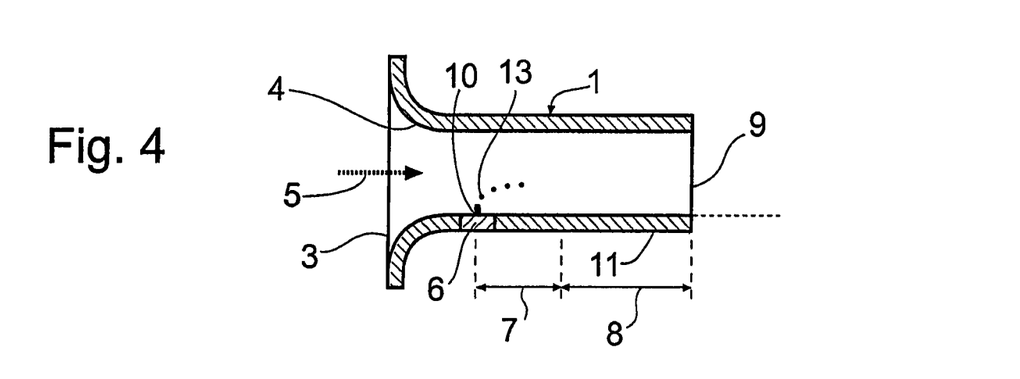

The embodiment according to FIG. 4 differs from that of FIG. 2 only in that the mixing zone 7 and the end zone 8 do not diverge but rather have a constant passage cross section over their entire length. This constant passage cross section is somewhat greater than the passage cross section of the constriction 14 of the mixing channel 1 illustrated in FIG. 2. This embodiment functions in more or less the same way as the embodiment according to FIG. 3.

Figure 5:
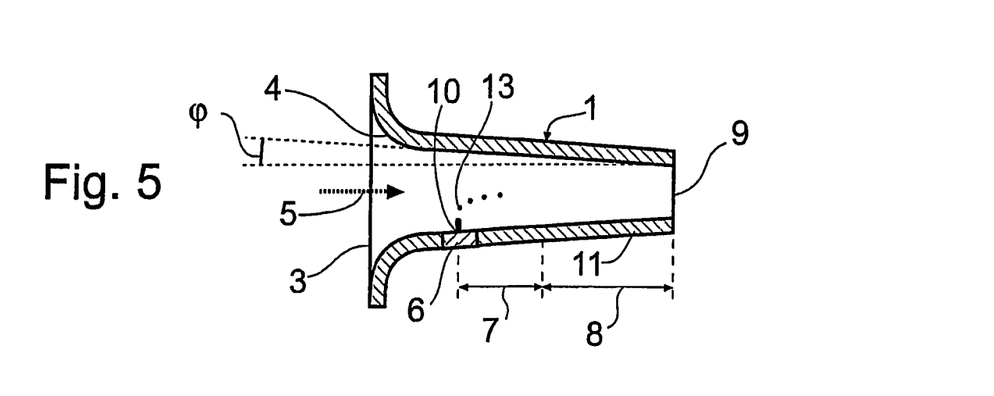

The embodiment according to FIG. 5 differs from that of FIG. 2 in that the passage cross section of the mixing channel 1 converges over its entire length. The mixing channel 1 initially converges like a trumpet until about the middle of the inlet zone 4 and then converges linearly at a negative angle φ relative to the longitudinal center axis of the mixing channel 1. In addition, the narrowest point of the mixing channel 1 is located at its end in the outlet 9. The negative angle φ can be between 0° and −77° and is preferably between 0° and −50°. In the embodiment illustrated here, it is about −5°. Up to the greatest negative angle $\phi$ of −77°, the air stream does not separate from the channel wall, so that coalescence of the droplets 13 due to air turbulence is avoided.

The narrowing at the outlet 9 is again somewhat greater than the constriction 14 in FIG. 2, but it is sufficiently large to prevent coalescence of the droplets 13 and their adherence in the oral cavity and the throat. A predetermined direction is imparted to the aerosol by the narrowing.

Figure 6:
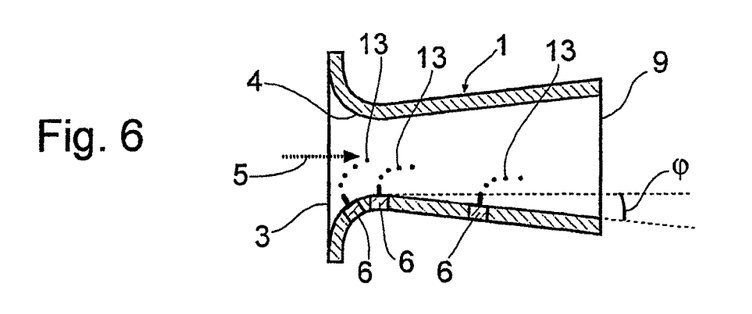
Figure 7:
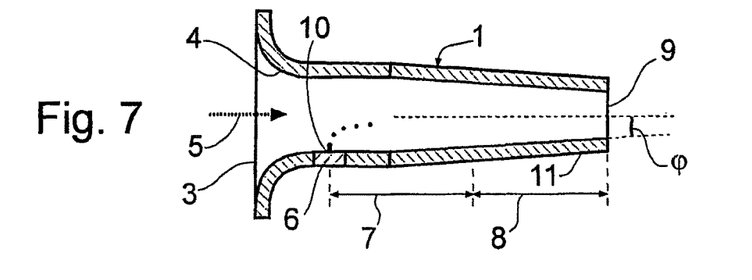
Figure 8:
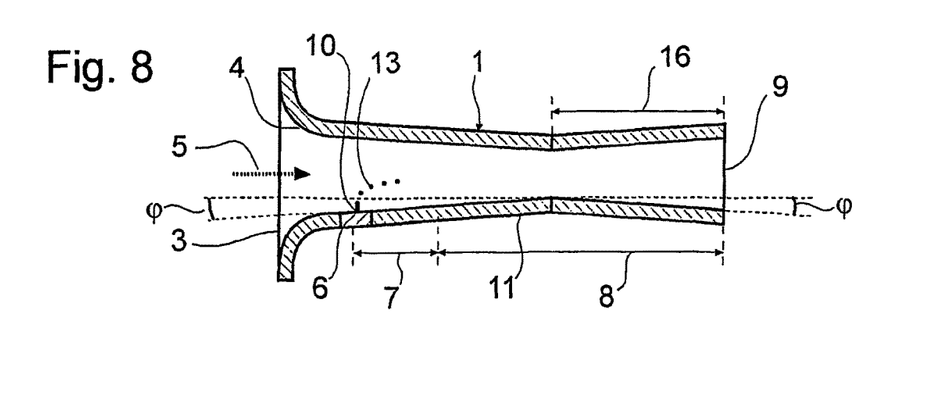
Figure 9:
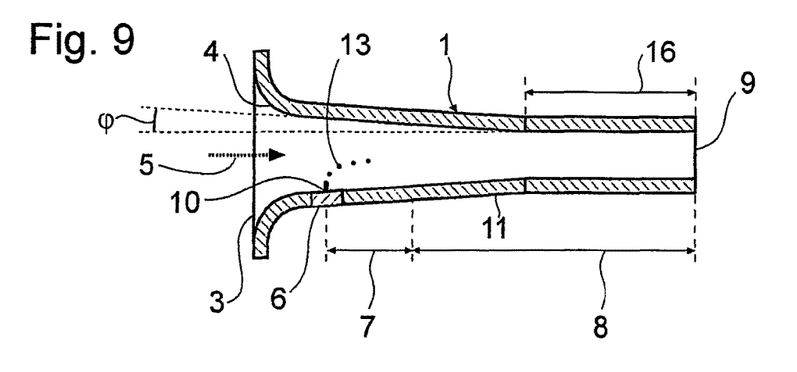
FIG. 9 is a view of a vertical section through the longitudinal center axis of a tenth embodiment of a mixing channel of the invention.
Figure 10:
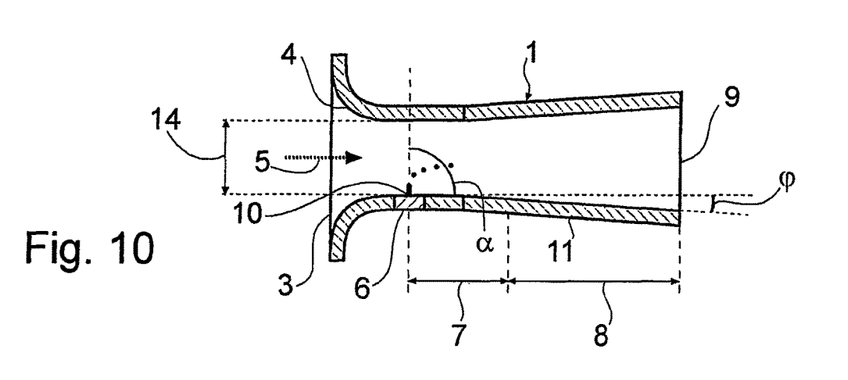
FIG. 10 is a view of a vertical section through the longitudinal center axis of an eleventh embodiment of a mixing channel of the invention.
Figure 11:
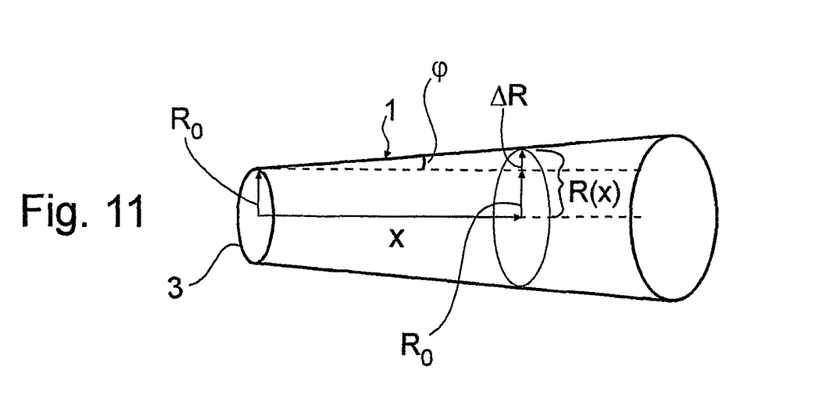
FIG. 11 is a schematic perspective drawing of an embodiment of a mixing channel of the invention for explaining the possible change in area of the passage cross section of an embodiment of the mixing channel of the invention.

FIG. 6 represents three embodiments, in which only the position of the injection zone 6 is shifted relative to the position of the injection zone 6 according to FIG. 2. The manner of functioning remains essentially the same as that of the embodiment according to FIG. 2, except that in the embodiment in which the injection zone is located farthest to the left, the discharge direction of the jet 13 is inclined obliquely to the direction of flow of the air 5 or to the longitudinal center axis of the mixing channel or to the inlet 3, and in the embodiment in which the injection zone 6 is located farthest to the right, the discharge direction of the jet 13 is inclined towards the outlet 9. In the embodiment in which the injection zone 6 is located farthest to the left, the jet 13 is already broken up into droplets at an early point in time, and in the embodiment in which the injection zone 6 is located farthest to the right, the jet 13 is better enveloped by the stream of air, so that the droplets are prevented with a greater degree of reliability from flying against the channel wall.

The embodiment according to FIG. 7 differs from that of FIG. 2 in that after the trumpet-like reduction of the passage cross section in the inlet zone 4, the passage cross section remains constant over the injection zone 6 and well into the mixing zone 7 and then continuously converges at an angle $\phi$ of about −5° to the longitudinal center axis of the mixing channel until the outlet 9. The manner of functioning is essentially the same as that of the embodiment illustrated in FIG. 5.

The embodiment according to FIG. 8 differs from that of FIG. 5 in that the end zone 8 is extended by a section 16 that diverges at an angle of about 5°, so that the flow rate of the aerosol in section 16 becomes smaller again, and coalescence and adherence of droplets 13 in the oral cavity is more reliably prevented.

In the embodiment according to FIG. 9, the section 16 differs from that of FIG. 8 in that it has a constant passage cross section. As a result, the aerosol is further conveyed at high velocity and is discharged at high velocity from the outlet 9 in a predetermined direction, so that it does not adhere in undesired places but rather is conveyed as quickly as possible towards the lungs.

In the embodiment according to FIG. 10, the constriction 14 with constant passage cross section extends approximately as far or even slightly farther into the mixing zone 7 than in the embodiment shown in FIG. 7. After the constriction 14, the passage cross section makes a transition to a diverging section, not continuously, but rather in the form of a discontinuity at an angle $\phi$ of about 5°. In this embodiment as well, the manner of functioning is essentially the same as that of the embodiment according to FIG. 2. However, the transition from $\phi=0°$ to $\phi=5°$ can also be rounded. This also applies to the transition of the angle $\phi$ in the embodiments according to FIGS. 7, 8, and 9.

Therefore, the angle $\phi$ can lie in the range of −77° to +24°, preferably in the range of −50° to +14° or +10°, and even more preferably in the ranges of 0° to +10° or +5° or of −50° to 0°. In this regard, as FIG. 11 shows, the area A(x) of the passage cross section of the mixing channel 1 at distance x from the inlet 3, as measured in the direction of flow, varies independently of the contour of the passage cross section, just as in the case of a hollow conical frustum, in which the area of the passage cross section at the inlet 3 corresponds to that of a circle with radius $R_0$ and the half aperture angle corresponds to the angle $\phi$. At point x, the radius is then $$R(x)=R_0+\Delta R \quad (1)$$

where ΔR is the increase in the radius at point x. Therefore, $$\Delta R=x \tan \phi \quad (2)$$

and $$A(x)=\pi(R_0+\Delta R)^2 \quad (3)$$

$$A(x)=\pi(R_0+x \tan \phi)^2 \quad (4)$$

or $$A(x)=\pi(R_0^2+2R_0x \tan \phi+x^2 \tan^2\phi) \quad (5)$$

The change in the area A(x) in direction x is then $$\begin{aligned} dA(x)/dx &= 2\Pi R_0\tan\varphi + 2\Pi x\tan^2\varphi && (6)\\ &= 2\Pi R_0\tan\varphi(R_0 + x\tan\varphi) && (7)\\ &= 2\Pi R(x)\tan\varphi && (8)\end{aligned}$$

At any given point x, the area A(x) of the passage cross section is $$A(x)=\pi R(x)^2 \quad (9)$$

where $$R(x)=\sqrt{A(x)/\pi} \quad (10)$$

Therefore $$dA(x)/dx=2\pi\sqrt{A(x)/\pi}\cdot\tan \phi \quad (11)$$

$$=2 \tan \phi\sqrt{A(x)\cdot\pi} \quad (12)$$

This means that the flow in the mixing channel 1 is free of separation and turbulence at each point x of the mixing channel 1 with area A(x), when the change in area in direction x, i.e., dA(x)/dx at each point x, is kept smaller than $2 \tan \phi\sqrt{A(x)\cdot\pi}$ and $\phi$ is kept in the range of −77° to +24° or +14°, preferably in the range of −50° to +5°, more preferably further narrowed between −77° and 0° or between 0° and +10°, and especially between −50° and 0° or between 0° and +5°. To express it in a different way: The change can be between $-c_1\sqrt{A(x)}$ and 0 or between 0 and $c_2\sqrt{A(x)}$, where, with the specified dimensional values for $\phi$, the following values are obtained for $c_1$ and $c_2$: $c_1$=15.35 (at −77°) or 4.22 (at −50°) and $c_2$=1.58 (at 24°) or 0.88 (at 14°) or 0.63 (at 10°) or 0.31 (at 5°).

If the passage cross section of the mixing channel 1 is not circular, the change in area A(x) cannot be calculated by Equation (8). However, for each passage cross section, a corresponding radius R(x) for a circular passage cross section can be calculated, as according to Equation (10). This radius R(x) can then be used to keep the flow in the mixing channel 1 free of separation and turbulence at each point x of the mixing channel 1 with area A(x). In this case as well, the change in area in direction x, i.e., dA(x)/dx at each point x, is between $-c_1\sqrt{A(x)}$ and 0 or between 0 and $c_2\sqrt{A(x)}$, where, with the specified dimensional values for 2, the following values are obtained for $c_1$ and $c_2$: $c_1$=15.33 or 4.22 and $c_2$=1.58, 0.88, 0.63, or 0.31.

Figure 12:
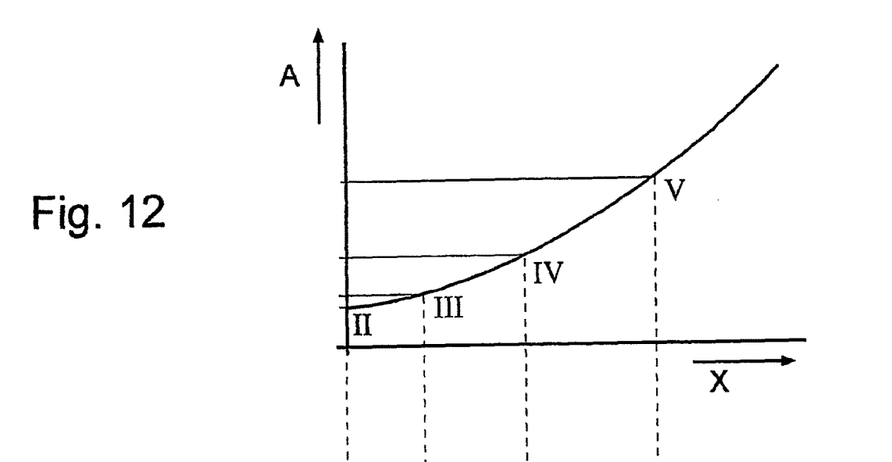
FIG. 12 is a graph of the area A of an embodiment of a mixing channel of the invention as a function of the distance x from the smallest passage cross section of a mixing channel of the invention.
Figure 13:
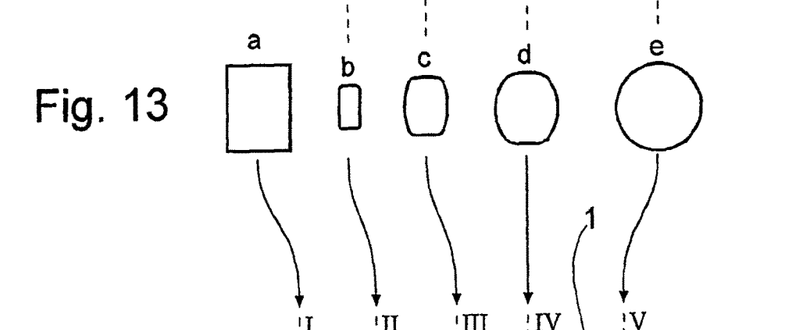
FIG. 13 are schematic representations of various shapes a to e of the passage cross section of a preferred embodiment of a mixing channel of the invention, which is shown in FIG. 14.

FIG. 12 illustrates the dependence of the area A of the passage cross section on x according to Equation (5). In this connection, the contour or shape of the area A or of the passage cross section can vary as illustrated in FIGS. 13a to 13e, i.e., the passage cross section of the mixing channel 1 can continuously decrease in successive longitudinal sections from a rectangular shape at the inlet 3 to a rectangular shape with rounded corners across the injection zone 6, and it then makes a transition from rectangular shapes with rounded corners and outwardly arched sides to a circular shape.

Figure 14:
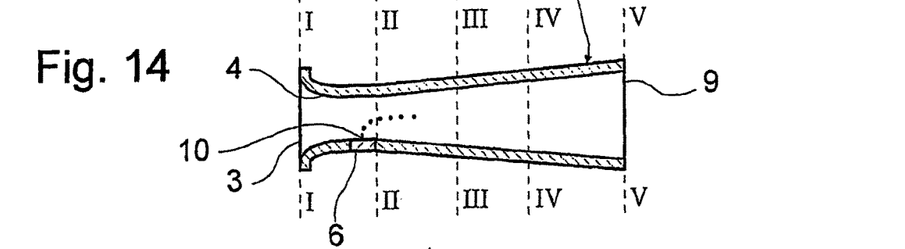
FIG. 14 is a schematic view of the vertical section of the preferred embodiment of the invention.
Figure 15:
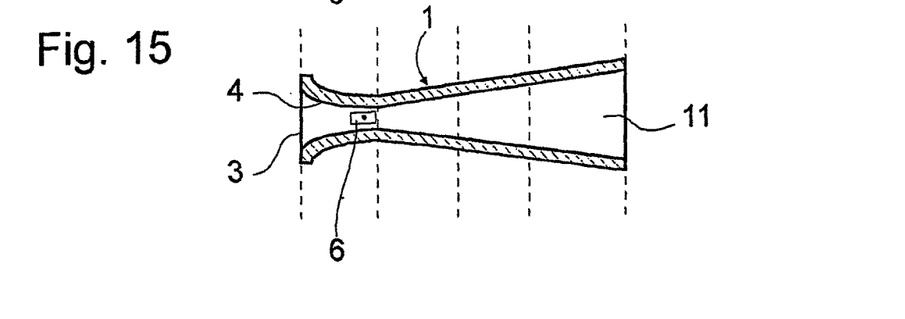
FIG. 15 is a view of the vertical section of the mixing channel of FIG. 14 rotated 90° about the longitudinal center axis relative to the view shown in FIG. 14.

A suitable mixing channel 1 is shown in FIG. 14 in a vertical longitudinal section and in FIG. 15 in a horizontal cross section, in each case through the longitudinal center axis, wherein the cross sections at the respective points with the area shapes according to FIGS. 13a to 13e are designated with the Roman numerals I to V, and the associated areas of the cross sections II to V in the graph according to FIG. 12 are designated with the Roman numerals II to V.

The shaping of the passage cross sections makes it possible for the passage cross section in the injection zone to be optimally adapted to the injection of the monodisperse aerosol, namely, rectangular with round corners, circular at the outlet 9, so that it is adapted to the mouth of the patient, and increasing in size in the transition zones in order to reduce the velocity of the aerosol.

Figure 16:
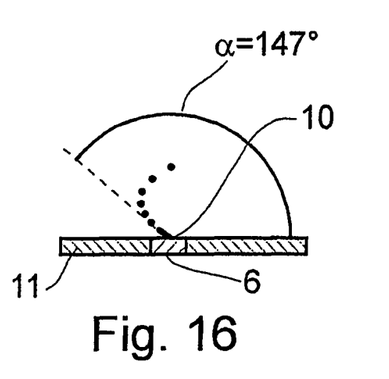
FIGS. 16 to 19 show sections of a channel wall of other embodiments of mixing channels of the invention.
Figure 17:
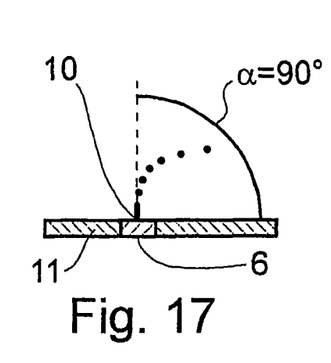
Figure 18:
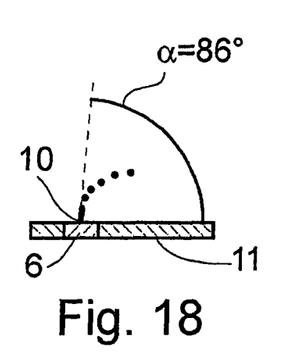
Figure 19:
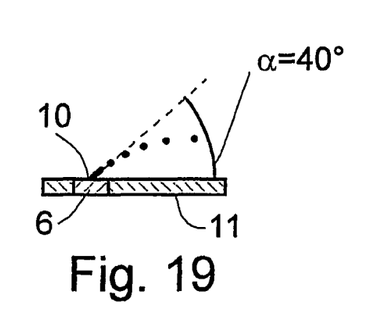

FIGS. 16, 18, and 19 illustrate on the basis of a section of the lower channel wall 11 that the liquid jet can emerge initially not only perpendicularly to the upper surface of the injection zone 6, as shown in FIG. 17, but also at other angles α to a tangent to the injection zone 6, especially when the injection zone 6 is designed as a nozzle plate, in which the direction of the channel leading to the nozzle orifice 10 (or when several nozzle orifices 10 are present, the discharge direction of the channels leading to the nozzle orifices) can be more simply designed. This angle α can be in the range of 10° to 170° and, specifically, independently of the angle φ.

Figure 20:
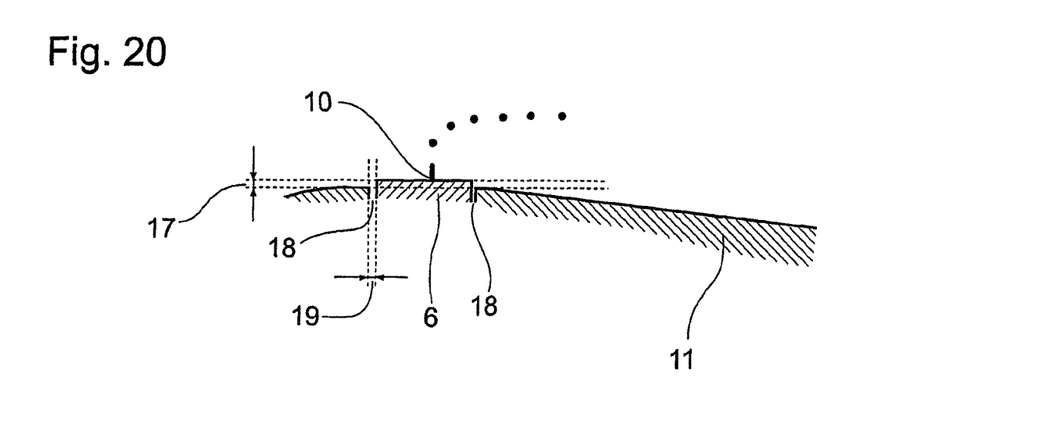
FIG. 20 is an enlarged section of the lower wall of the mixing channel, into which an injection zone in the form of a nozzle plate is inserted in a way that does not exactly fit.

If the injection zone 6 is separately formed as a nozzle plate and is inserted in a through-hole or a depression in the channel wall 11 in such a way that it is not exactly flush with the inner surface of the channel wall 11, it may happen that the nozzle plate 6, as shown in the enlarged mixing channel section according to FIG. 20, projects slightly above the inner surface of the channel wall 11 or lies slightly too deep in the hole or in the depression. This has a less adverse effect on separation-free flow of the stream of air if the height difference 17 is less than 1 mm, and preferably less than 100 µm or 20 µm. Similarly, a lateral gap 18 between the wall of the hole or depression and the nozzle plate 6 should be less than 500 µm and preferably less than 100 µm to maintain air flow that is free of separation in the mixing channel.

Figure 21:
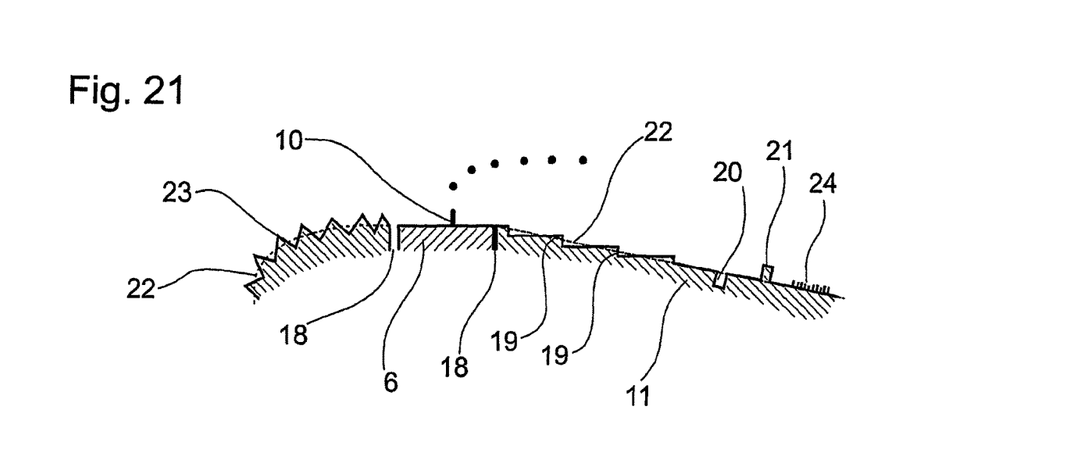
FIG. 21 is an enlarged section of the lower channel wall, whose surface is microtextured outside of the injection zone.

The enlarged section of the mixing channel according to FIG. 21 illustrates another modification of a mixing channel of the invention, in which the inner surface of the channel wall 11 is microtextured. The microtexturing can consist in a course 19 of the inner surface with tiny steps or grooves 20, projections 21, saw teeth 23 or microfibers 24, which on average produce the desired mean surface curvature 22 indicated by the dot-dash line. This significantly reduces the air flow resistance of the inner surface of the mixing channel.

Figure 22:
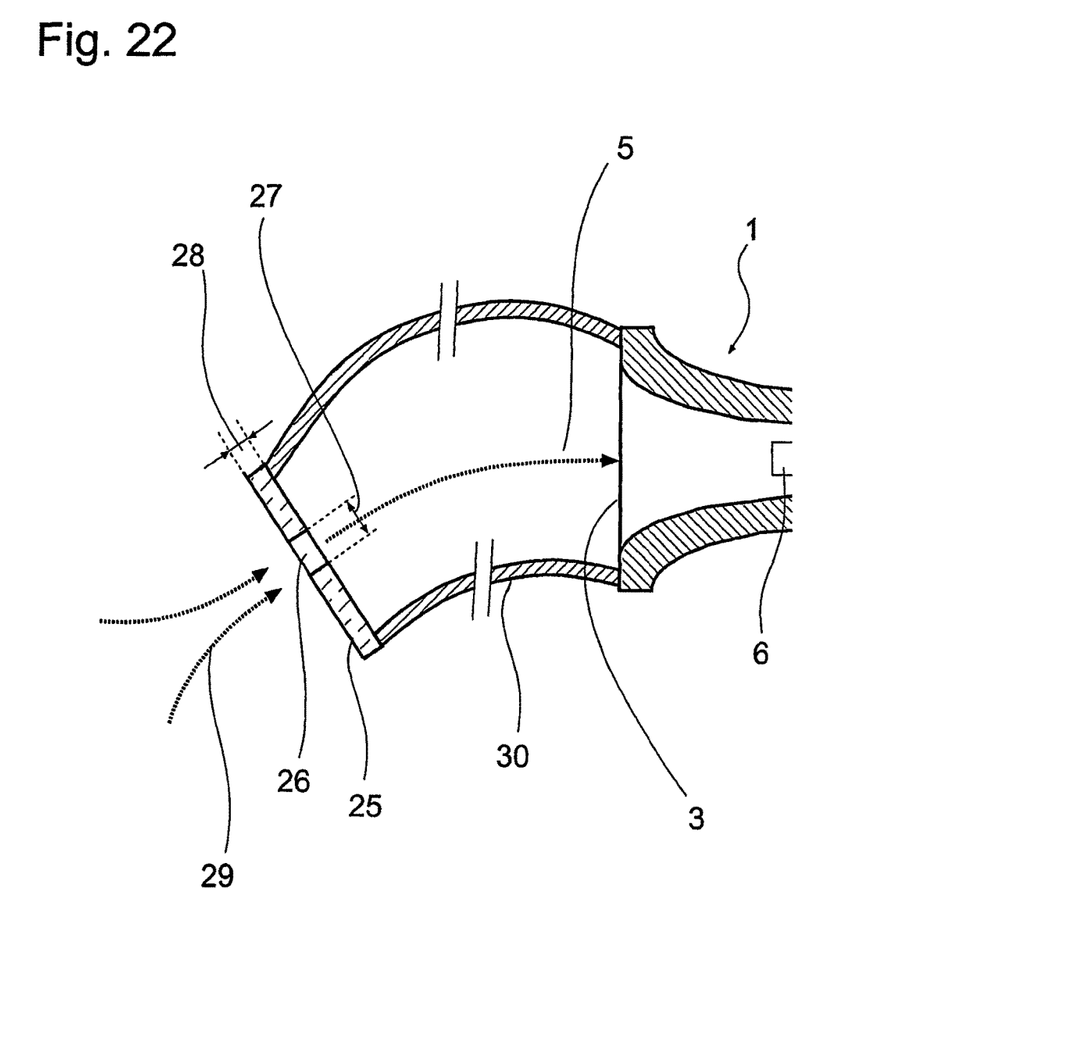
FIG. 22 is a vertical section through another embodiment of a mixing channel of the invention.

In another advantageous refinement, which is shown in FIG. 22, an air flow resistor 25 in the form of a perforated plate with a circular hole 26 in the center is installed on or in front of the inlet 3. The diameter 27 of the hole is 1 to 12 mm and preferably 4 to 8 mm. The length 28 of the hole 26 is as short as possible, preferably less than half the diameter 27. The length 28 is preferably 0.1 to 1 mm.

If the air flow resistor 25 is not directly formed or mounted on the inlet 3 in an airtight way, it can be joined with the inlet 3 by a curved connecting tube 30, e.g., a part of a housing (not shown) of the mixing channel, to prevent the entrance of air 29 between the air flow resistor 25 and the inlet 3. The essential consideration is that the entire volume of air 29 that is drawn in must flow through the hole 26.

With the specified dimensions of the hole 26, the flow rate increases nonlinearly with the square root of the pressure or, more precisely, the difference of the pressures before and after the hole. At normal suction pressure of only about 2 to 4 kPa, the flow rate of the air in the hole 26 and the mixing channel varies almost linearly, but then it increases less than proportionally with increasing suction pressure, and finally, as the suction pressure increases further, it shows hardly any change, which corresponds more or less to a limitation of the flow rate. In other words, when the patient applies low suction pressure, the flow rate through the flow resistor 25 is barely reduced, whereas when maximum suction pressure is applied, a lower flow rate is produced than would be produced without the flow resistor 25.

This gives the patient a better feeling as he draws air into the inhaler, and the flow rate depends less on the patient than on the design of the inhaler. The patient can draw the air uniformly for a prolonged period of time.

Instead of the circular hole 26, an angular hole can also be provided, especially a square, triangular, or slot-shaped hole. It is also possible to provide several holes in circular or angular form if their total flow resistance is essentially the same as the flow resistance produced by the single circular hole 26. In addition, instead of the curved connecting tube 30, a part of the housing or a straight tube can be used.

In other possible modifications of the embodiments of the invention, the injection zone 6 (with the mixing channel 1 in a horizontal attitude) can be located above the longitudinal center axis or in the side wall of the mixing channel 1, or opposing injection zones 6 can be provided. If the injection zone is located at the top, the metering unit 2 is also mounted on top. If several injection zones are present, preferably only one metering unit 2 is provided, which is connected with the injection zones by channels.

Figure 24:
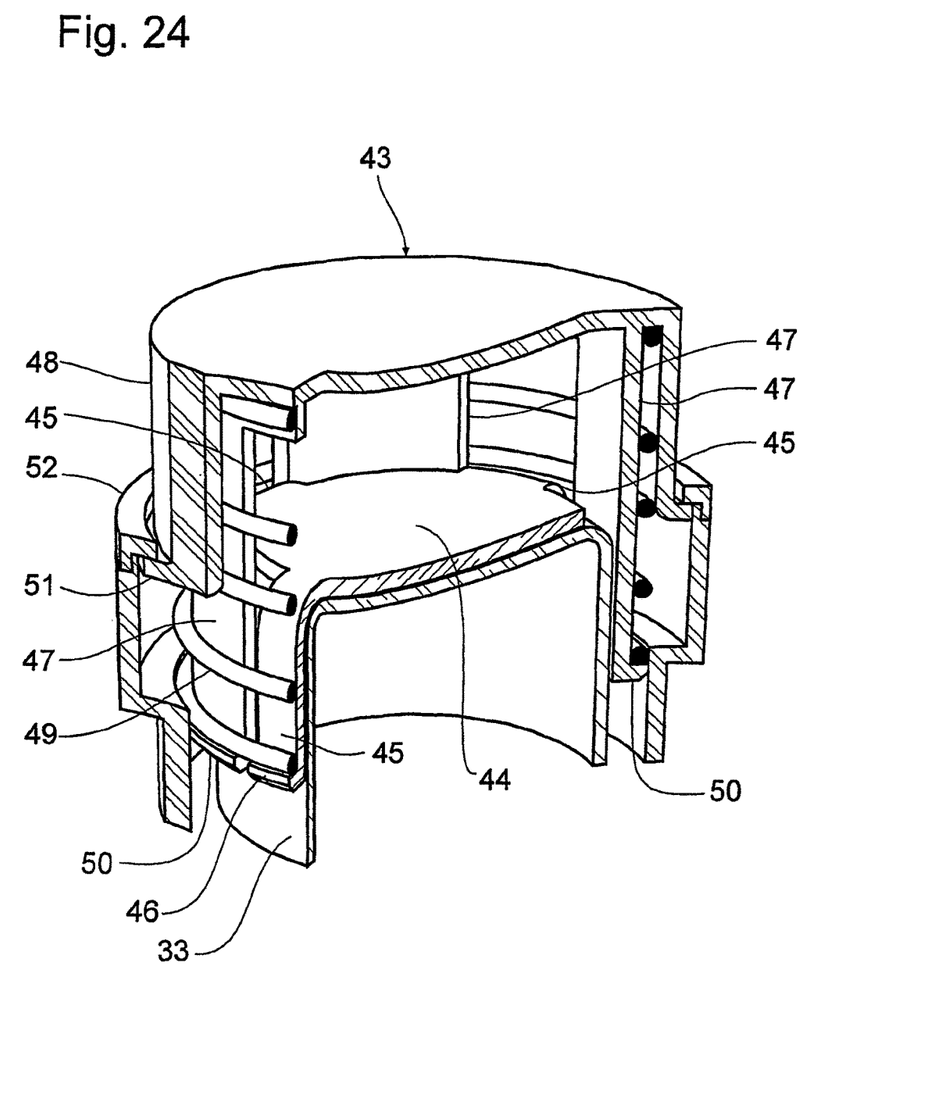
FIG. 24 is a perspective view of a section of the inhaler of FIG. 23.

FIG. 23 shows an axial section of an embodiment of a complete inhaler of the invention on an enlarged scale compared to the actual size of the inhaler, and FIG. 24 shows a perspective cutaway view of the upper part of the inhaler on a still larger scale.

The illustrated inhaler consists of the mixing channel 1 according to FIG. 2 and the metering unit 2 according to FIG. 1, i.e., the metering unit 2 is mounted on top of the mixing channel 1 in FIG. 23. However, in contrast to FIG. 2, the mixing channel 1 has a flow resistor 25 according to FIG. 22 in the form of a perforated plate on the inlet 3, but in this case the perforated plate has several holes 26 instead of only one hole.

The metering unit 2 has a housing 31, in which the mixing channel 1 and a reservoir 33 that holds the liquid 32 are installed. The reservoir 33 is tightly sealed by a closure device 34 with a gasket 35. The cylinder 36 of a piston-cylinder unit is tightly mounted in the closure device 34 and extends into the reservoir 33. The piston rod 37 of the piston 38 of the piston-cylinder unit is passed through the closure device 34 in a way that allows it to move axially and is mounted in the housing 31 by means of a mounting unit 39. An outlet channel 40, which extends to the injection zone 6 of the mixing channel 1, passes through the piston 38 and the piston rod 37. The closure device 34 is supported by another spring mechanism in the form of a restoring spring 41.

An actuator 43 is located some distance from the base 42 of the reservoir 33. The upper side of the actuator 43 serves as a pressure surface for manually applying pressure to the actuator 43 to operate the metering unit 2. A flat shell 44 rests on the base 42 of the reservoir 33, and at the edge of the flat shell 44, brackets 45 that lie along the outside of the reservoir 33 (see also FIG. 24) are bent down. Each bracket has a flange 46 at its free end. Brackets 47, which project from the inner surface of the actuator 43, are movably supported between the brackets 45 of the shell 44. A spring mechanism 49, here in the form of a helical compression spring (helical spring), is mounted between the brackets 47 and a cylindrical wall of the actuator 43. This spring mechanism 49 surrounds the brackets 45 and 47 and is supported on the flanges 46 of the brackets 45 and flanges 50 of the brackets 47. The actuator 43 is movably supported in the housing 31 with a peripheral flange 51, which rests against a ring 52 under the compression of the spring mechanism 49. The ring 52 is mounted on the housing 31 and surrounds the wall 48 of the actuator 43 with some clearance (see FIG. 24).

The pressure chamber 53 of the cylinder 36 is connected with the interior of the reservoir 33 by a hole 54 in its wall, a valve system 55 in a cylindrical extension 56 of the cylinder 36, and an immersion tube 57 mounted in the extension 56. In the position of the metering unit 2 shown in FIG. 1, i.e., below the mixing channel 1, the free end of the immersion tube 57 dips into the liquid 32, and the piston 38 can suck the liquid 32 into the pressure chamber 53 through the immersion tube 57 and the valve system 55. By contrast, in the position of the metering unit shown in FIG. 23, the liquid 32 can flow through the hole 54 into the pressure chamber 53 of the cylinder 36 and fill the pressure chamber 53 and the outlet channel 40 as far as a valve shutter 59 that blocks the outlet channel 40 under the pressure of a spring 58.

When pressure is applied to the pressure surface of the actuator 43 with the index finder or thumb against the pressure of the thumb or index finger placed in a housing recess 60, the actuator 43 is pressed against the force of the spring mechanism 49 until the flange 51 of its arms 48 comes to rest against an inner shoulder 62 of the housing 31, and the spring mechanism 49 is compressed, but at first the reservoir 33, including its closure device 34, is not moved as far as the actuator 43 relative to the housing 31. The reservoir 33 and the closure device 34 initially move against the force of the spring 41, which is weaker than the spring mechanism 49, relative to the piston 38, which is mounted stationary with respect to the housing, only until the piston 38 has traveled beyond the hole 54 or the hole 54 has traveled beyond the piston 38. At this instant, the liquid in the pressure chamber 53 is pressurized, and the valve system 55 is closed, whereas the valve shutter 59 is moved against the force of the spring 58 into the open position, in which it has traveled over a hole 61, which forms part of the outlet channel 40. However, the actuator 43 continues to be pressed down by the user's hand, so that now the reservoir 33 and the closure device 34 are moved relative to the stationary piston 38 by the relaxing spring mechanism 49 but only very slowly to the extent that the liquid can be discharged into the mixing channel 1 in the injection zone 6 through the nozzle orifice 10, which is very narrow and thus acts as a throttle valve. Consequently, the pressure under which and the velocity at which the liquid is injected into the mixing channel 1 are largely independent of the force and speed with which the actuator 43 is manually operated. Instead, the pressure on the liquid and the velocity of the liquid during injection and the duration of the injection into the mixing channel 1 depend essentially only on the force of the spring mechanism 49, which can be closely adjusted to the force necessary to maintain a desired inhalation duration of about 0.5 to 10 seconds and a corresponding velocity of the jet 13. The user thus has less influence on the actuation pressure, which makes the inhaler easier to use.

After the pressure chamber 53 of the cylinder 36 has been emptied, the manual pressure on the actuator 43 is removed, so that the spring mechanism 49 of the actuator 43 and the spring 41 restore the closure device 34 together with the reservoir 33 to their illustrated initial positions, from which the next actuation can be carried out. During this restoration movement, the spring 58 pushes the valve shutter 59 back into the illustrated closed position to prevent liquid 2 from being sucked back into the cylinder 36.

Instead of the illustrated spring mechanism 49, a different spring mechanism can be used, or the spring mechanism can be mounted differently. For example, the reservoir 33 itself can be designed as a spring mechanism, for example, in such a way that it is completely elastically designed or only part of its wall is elastically designed and/or the reservoir 33 is supported by its opening edge, which is located at the bottom in FIG. 23, on an elastic or elastically yielding part in the closure device 34. In this case, the base of the reservoir 33 can form the actuator, so that the actuator 43, the shell 44 and the spring mechanism 49 are eliminated.

In another alternative, the spring mechanism 49 is mounted directly between the bases of the actuator 43 and the shell 44. The spring mechanism 49 can also be mounted directly between the base of the actuator 43 and the base 42 of the reservoir 33, so that the shell 44 is eliminated. Last but not least, instead of the spring mechanism 49, a compression spring can be mounted between the inner surface of the base 42 of the reservoir 33 and a supporting surface formed on the immersion tube 57, so that again the actuator 43, the shell 44 and the spring mechanism 49 can be eliminated, and the base 42 of the reservoir 33 forms the actuator.

The metering unit 2 can consist not only of a conventional pump but also of other suitable devices that are capable of producing the desired volume of liquid with the necessary pressure. A preferred alternative is a cartridge metering unit with a cartridge and a spring for automatic metering of the liquid (of the desired drug or a liquid medium for treating the mouth, throat, or lungs). In this regard, the metering unit and the injection zone are connected with each other by a channel. The channel is preferably a tube or hose or a channel formed in the housing of the mixing channel. If a cartridge metering unit is used, the mixing channel can be formed as an extension of the metering unit, so that the two form an elongated holder in so-called pen form.

The invention claimed is:

1. An inhaler with a mixing channel (1) for producing an aerosol to be inhaled, where the mixing channel has: an outlet (9) at one end that can be inserted in the mouth of a person in order to inhale the aerosol that is produced; at least one inlet (3) at its other end for drawing air into the mixing channel (1); and at least one injection zone (6) that lies between the inlet (3) and the outlet (9) and forms part of the channel wall, where the injection zone (6) has at least one nozzle orifice (10) in the channel wall for supplying a liquid, wherein an inner surface of the injection zone (6) is substantially flush at least with a portion of a mean surface curvature (22) of an inner surface of the channel wall (11) that is adjacent to it on the inlet end, where a possible height difference (17) between the inner surface of the injection zone (6) and that portion of the mean surface curvature (22) of the inner surface of the channel wall (11) that is adjacent to it is less than 1 mm or at most 100 µm or at most 20 µm, wherein the nozzle orifice defines a single lumen opening so that only the liquid passes through the orifice into the mixing channel in the form of one jet of dispersed droplets (13) per nozzle orifice (10) so as to entrain the droplets (13) with the stream of intake air and keep them separated in an end zone (8) between the injection zone (6) and the outlet (9) after the droplets (13) have been mixed with the stream of air to form the aerosol, the channel wall only having the at least one single lumen nozzle orifice for the liquid, wherein the at least one single lumen nozzle orifice has a peripheral edge contiguous with the channel wall.

2. An inhaler in accordance with claim 1, wherein the area A(x) of the passage cross section of the mixing channel (1) varies in an air flow direction x, independently of the contour of the passage cross section, in such a way that the change dA(x)/dx at each point x is between $-c_1\sqrt{A(x)}$ and 0 or between $c_2\sqrt{A(x)}$ and 0, where $c_1$=15.35 or 4.22, and $c_2$=1.58 or 0.88 or 0.31.

3. An inhaler in accordance with claim 1, wherein the mixing channel (1) diverges and/or converges linearly or nonlinearly beyond the injection zone (6) or runs parallel to the longitudinal center axis.

4. An inhaler in accordance with claim 1, wherein the mixing channel (1) converges in a section that extends beyond the injection zone (6) and then diverges downstream of the convergent section.

5. An inhaler in accordance with claim 1, wherein the mixing channel (1) converges like a trumpet-shape from the inlet (3) to the injection zone (6).

6. An inhaler in accordance with claim 5, wherein an axial section contour of the inner surface of the section of the channel wall that converges like a trumpet corresponds to the curve of a parabola of third degree, at least above and below the longitudinal center axis.

7. An inhaler in accordance with claim 1, wherein the passage cross section of the mixing channel (1) continuously decreases in successive longitudinal sections from a rectangular shape at the inlet (3) to a rectangular shape with rounded corners across the injection zone (6), and it then makes a transition from rectangular shapes with rounded corners and outwardly arched sides to a circular shape.

8. An inhaler in accordance with claim 1, wherein the jet emerges from the injection zone (6) at an angle $\alpha$ to a tangent to the injection zone of 10 to 170°, and that the jet has an initial inclination to the outlet (9) of $\alpha<90°$ and an initial inclination to the inlet (3) of $\alpha>90°$.

9. An inhaler in accordance with claim 8, wherein the angle $\alpha$ is of 10 to 90°.

10. An inhaler in accordance with claim 8, wherein the angle $\alpha$ is of 90 to 170°.

11. An inhaler in accordance with claim 1, wherein the length of a mixing zone (7) that follows the injection zone (6) in the axial direction of the mixing channel (1) is 1 to 200 mm.

12. An inhaler in accordance with claim 11, wherein the length of an end zone (8) that follows the mixing zone (7) is 2 to 3 times the length of the mixing zone (7).

13. An inhaler in accordance with claim 1, wherein the area of the passage cross section of the mixing channel (1) at the end of an inlet zone (4) that extends to the injection zone (6) is 1 to 1,000 $mm^2$.

14. An inhaler in accordance with claim 13, wherein the area of the passage cross section is 5 to 200 $mm^2$.

15. An inhaler in accordance with claim 14, wherein the area of the passage cross section is 10 to 20 $mm^2$.

16. An inhaler in accordance with claim 1, wherein the injection zone (6) is formed by a nozzle plate.

17. An inhaler in accordance with claim 1, wherein the mixing channel (1) contains plastic with or without an antibacterial or electrically conductive additive or coating.

18. An inhaler in accordance with claim 1, wherein the surface of the inside of the channel wall (11) is at least partially microtextured.

19. An inhaler in accordance with claim 1, wherein an air flow resistor (25) is installed on or in front of the inlet (3).

20. An inhaler in accordance with claim 19, wherein the air flow resistor (25) is a perforated plate with at least one hole.

21. An inhaler in accordance with claim 1, wherein a manually operated metering unit (2) for the liquid is provided on the mixing channel (1) and that it has a volume metering range of 1 to 300 microliters.

22. An inhaler in accordance with claim 21, wherein the metering unit (2) has a piston-cylinder system (36, 38) for applying pressure to the liquid (32) to be injected into the mixing channel (1) and an actuator (43) that can be moved by manual pressure, whose actuation distance can be converted by a spring mechanism (49) to relative movement between the piston (38) and the cylinder (36) of the piston-cylinder system.

23. An inhaler in accordance with claim 22, wherein the cylinder (36) is tightly mounted in a closure device (34) of a reservoir (33) that contains the liquid (32) and extends into the reservoir (33); a piston rod (37) of the piston (38) is passed through the closure device (34); that an outlet channel (40) that extends to the injection zone (6) is passed through the piston (38) and the piston rod (37); that the piston rod (37) is mounted in a housing (31) that displaceably holds the closure device (34); the actuation distance of the actuator (43) can be transferred to the closure device (34) by the spring mechanism (49) against the force of another spring mechanism (41), so that the closure device (34) is moved relative to the piston (38); a pressure chamber (53) of the cylinder (36) in the unactuated state of the actuator (43) is connected with the interior of the reservoir by at least one hole (54) in the wall of the cylinder (36) and by a valve system (55); and the hole(s) (54) in the wall of the cylinder (36) and the valve system (55) are blocked during the operation of the actuator (43) after the piston (38) has traveled beyond the hole(s) (54) in the wall of the cylinder (36).

24. An inhaler in accordance with claim 1, wherein the length of a mixing zone that follows the injection zone in the axial direction of the mixing channel is 1 to 50 mm.

* * * * *